(12) United States Patent
Dumas et al.

(10) Patent No.: US 11,878,103 B2
(45) Date of Patent: Jan. 23, 2024

(54) METHODS, SYSTEMS, AND DEVICES FOR JOINT TO PUMP ELEVATION LEVEL USER INTERFACES, AUTOCALIBRATION FOR JOINT ELEVATION, AND JOINT PRESSURE ESTIMATION

(71) Applicant: Medos International Sarl, Le Locle (CH)

(72) Inventors: Oliver Dumas, East Sandwich, MA (US); Eduard Grinberg, Sharon, MA (US); Andre Francisco Guilherme, Raynham, MA (US); Michael Confoey, Westwood, MA (US); Jacob A. Marks, Foxboro, MA (US)

(73) Assignee: Medos International Sarl, Le Locle (CH)

( * ) Notice: Subject to any disclaimer, the term of this patent is extended or adjusted under 35 U.S.C. 154(b) by 324 days.

(21) Appl. No.: 17/109,399

(22) Filed: Dec. 2, 2020

(65) Prior Publication Data
US 2021/0085840 A1   Mar. 25, 2021

Related U.S. Application Data

(63) Continuation of application No. 16/114,510, filed on Aug. 28, 2018, now Pat. No. 10,874,776.
(Continued)

(51) Int. Cl.
*A61M 3/02* (2006.01)
*A61M 1/00* (2006.01)
*A61B 17/00* (2006.01)

(52) U.S. Cl.
CPC ....... *A61M 1/732* (2021.05); *A61B 17/00234* (2013.01); *A61M 1/77* (2021.05);
(Continued)

(58) Field of Classification Search
CPC .... A61B 2217/007; A61M 2205/3344; A61M 2205/502; A61M 3/0216;
(Continued)

(56) References Cited

U.S. PATENT DOCUMENTS

D276,819 S   12/1984   James
D278,804 S   5/1985   Tanikawa
(Continued)

OTHER PUBLICATIONS

U.S. Appl. No. 16/114,510, filed Aug. 28, 2018, Oliver Dumas et al.
(Continued)

*Primary Examiner* — Deanna K Hall (57) ABSTRACT

Various exemplary methods, systems, and devices for joint to pump elevation level user interfaces, autocalibration for joint elevation, and joint pressure estimation are provided. In general, an arthroscopic pump can be configured to estimate fluid pressure at a surgical site, e.g., at a joint, to provide an accurate indication of fluid pressure to users. In an exemplary embodiment, the fluid pressure estimation is based on a fluid pressure measurement at the pump that is adjusted at the pump, e.g., by a processor at the pump that executes instructions stored in a memory at the pump, using one or more control algorithms that adjust for one or more factors, such as pressure loss in tubing and sheath through which fluid flows between the pump and the surgical site and elevation difference between the pump and the surgical site.

20 Claims, 6 Drawing Sheets

Related U.S. Application Data (60) Provisional application No. 62/553,397, filed on Sep. 1, 2017.

(52) U.S. Cl.
CPC ........ *A61M 3/0202* (2021.05); *A61M 3/0216* (2014.02); *A61M 3/0258* (2013.01); *A61B 2017/00115* (2013.01); *A61B 2217/005* (2013.01); *A61B 2217/007* (2013.01); *A61M 2205/3344* (2013.01); *A61M 2205/502* (2013.01)

(58) Field of Classification Search
CPC .. A61M 2205/3362; A61M 2205/3348; A61M 2205/3331; A61M 1/00; A61M 3/0258; A61M 1/0058
See application file for complete search history.

(56) References Cited

U.S. PATENT DOCUMENTS

| | | | |
|---|---|---|---|
| D281,081 S | 10/1985 | Zwissler et al. | |
| 5,315,530 A | 5/1994 | Gerhardt et al. | |
| 5,520,638 A | 5/1996 | O'Quinn et al. | |
| 5,630,799 A | 5/1997 | Beiser et al. | |
| 5,830,180 A | 11/1998 | Chandler et al. | |
| 6,024,720 A | 2/2000 | Chandler et al. | |
| 6,176,847 B1 | 1/2001 | Humphreys, Jr. et al. | |
| 6,394,974 B1 | 5/2002 | Kadziauskas et al. | |
| 7,010,369 B2 | 3/2006 | Borders et al. | |
| D572,724 S | 7/2008 | Guimaraes et al. | |
| D572,725 S | 7/2008 | Guimaraes et al. | |
| 7,421,316 B2 | 9/2008 | Gray et al. | |
| 7,510,542 B2 | 3/2009 | Blight | |
| 7,604,610 B2 | 10/2009 | Shener et al. | |
| 7,628,054 B2 | 12/2009 | Hajishah et al. | |
| D611,498 S | 3/2010 | Alvarez | |
| 8,424,362 B2 | 4/2013 | Hajishah et al. | |
| 9,089,367 B2 | 7/2015 | Thoe et al. | |
| D738,928 S | 9/2015 | Mahaffey | |
| D738,929 S | 9/2015 | Mahaffey | |
| 9,162,023 B2 | 10/2015 | Barnes et al. | |
| D742,917 S | 11/2015 | Perez et al. | |
| 9,205,186 B2 | 12/2015 | Tarkeshian et al. | |
| 9,211,096 B2 | 12/2015 | Tremper et al. | |
| 9,289,110 B2 | 3/2016 | Woolford et al. | |
| 9,289,541 B2 | 3/2016 | Norman et al. | |
| 9,295,582 B2 | 3/2016 | Rockley et al. | |
| D759,063 S | 6/2016 | Chen | |
| 9,433,723 B2 | 9/2016 | Steen et al. | |
| D772,905 S | 11/2016 | Ingenlath | |
| 9,597,445 B2 | 3/2017 | Ha et al. | |
| D800,162 S | 10/2017 | Havranek, Jr. | |
| 9,830,424 B2 | 11/2017 | Dixon et al. | |
| D835,151 S | 12/2018 | Martin et al. | |
| D877,755 S | 3/2020 | Iida et al. | |
| D881,237 S | 4/2020 | Arima et al. | |
| D893,547 S | 8/2020 | Dumas et al. | |
| 10,874,776 B2 | 12/2020 | Dumas et al. | |
| 2003/0052787 A1 | 3/2003 | Zerhusen et al. | |
| 2005/0092523 A1 | 5/2005 | McCaskill et al. | |
| 2006/0290515 A1 | 12/2006 | Kankkunen et al. | |
| 2007/0078370 A1* | 4/2007 | Shener ............... | A61M 3/0258 604/8 |
| 2008/0243054 A1 | 10/2008 | Mollstam et al. | |
| 2010/0010584 A1 | 1/2010 | Skelton et al. | |
| 2010/0050085 A1 | 2/2010 | Blike et al. | |
| 2010/0069937 A1 | 3/2010 | Seto et al. | |
| 2012/0089419 A1 | 4/2012 | Huster et al. | |
| 2012/0130308 A1 | 5/2012 | Silkaitis et al. | |
| 2012/0138533 A1 | 6/2012 | Curtis et al. | |
| 2012/0302941 A1 | 11/2012 | Teodorescu et al. | |
| 2013/0317417 A1 | 11/2013 | Claus et al. | |
| 2014/0026322 A1 | 1/2014 | Bell et al. | |
| 2014/0171959 A1 | 6/2014 | Yacono | |
| 2014/0278524 A1 | 9/2014 | Vaglio | |
| 2015/0025450 A1 | 1/2015 | King et al. | |
| 2015/0057774 A1 | 2/2015 | Boukhny et al. | |
| 2015/0133895 A1 | 5/2015 | Klomp | |
| 2015/0277703 A1 | 10/2015 | Davis | |
| 2015/0290387 A1 | 10/2015 | Mollstam | |
| 2016/0030668 A1 | 2/2016 | Barnes et al. | |
| 2016/0346443 A1 | 12/2016 | Woolford | |
| 2016/0346454 A1 | 12/2016 | Woolford | |
| 2017/0157312 A1 | 6/2017 | Woolford | |
| 2017/0209639 A1 | 7/2017 | Wolter | |
| 2018/0184984 A1 | 7/2018 | Zerhusen et al. | |
| 2019/0070343 A1 | 3/2019 | Dumas et al. | |

OTHER PUBLICATIONS

U.S. Appl. No. 29/661,431, U.S. Pat. No. D. 893,547, Aug. 28, 2018, Oliver Dumas et al.
"Bed, hopsital, medical, patient, sick, treatment icon" Feb. 11, 2017, posted at iconfinder.com [site visited Apr. 14, 2020]. https://www.iconfinder.com/iconsets/medical-health-care-blue-series-set-1.
"Fluid Management System" Nov. 28, 2018, posted at a1medtech.com [site visited Dec. 2, 2019]. https://www.a1medtech.com/Fluid-Management-System_c_115.html.
"Hospital Bed Remote Control Panel stock photo" Jun. 11, 2012, posted at istockphoto.com [site visited Apr. 14, 2020]. https://www.istockphoto.com/photo/hopistal-bed-remote-control-panel-gm182153618-18921428.
Arthrex Continuous Wave III Arthroscopy Pump User's Guide, 2013 (52 pages).
Arthrex DualWave Arthroscopy Pump User's Guide, 2015 (60 pages).
Arthrex DualWave Quick Reference, brochure, 2015 (10 pages).
Arthrex Fluid Management, brochure, 2016 (8 pages).
ConMed 24k Pump Product Overview, web page, retrieved at <http://www.conmed.com/en/medical-specialities/orthopedics/fluid-management/fluid-management-systems/24k>, Aug. 29, 2017 (3 pages).
ConMed 24k Quick Set Up Guide, brochure, 2010 (4 pages).
DePuy Mitek K130169 501 (k) Summary, dated Jan. 22, 2013, decided May 1, 2013 (8 pages).
FMS VUE Fluid Management System & Tissue Debridement System, DePuy Synthes, brochure, 2014 (2 pages).
FMS VUE Fluid Management System & Tissue Debridement System, DePuy Synthes, web page, retrieved at <https://www.depuysynthes.com/hcp/mitek-sports-medicine/products/qs/FMS-VUE-Fluid-Management-Tissue-Debridement-System>, Aug. 28, 2017 (4 pages).
International Search Report and Written Opinion for International App. No. PCT/US18/48814 dated Nov. 15, 2018 (12 pages).
PowerPump System Operator's Manual, 2010 (32 pages).

\* cited by examiner

METHODS, SYSTEMS, AND DEVICES FOR JOINT TO PUMP ELEVATION LEVEL USER INTERFACES, AUTOCALIBRATION FOR JOINT ELEVATION, AND JOINT PRESSURE ESTIMATION

CROSS REFERENCE TO RELATED APPLICATIONS

This application is a continuation of U.S. patent application Ser. No. 16/114,510, now U.S. Pat. No. 10,874,776, filed on Aug. 28, 2018, and entitled "Methods, Systems, And Devices For Joint To Pump Elevation Level User Interfaces, Autocalibration For Joint Elevation, And Joint Pressure Estimation," which claims priority to U.S. Provisional Patent Application No. 62/553,397, filed on Sep. 1, 2017, and entitled "Methods, Systems, And Devices For Joint To Pump Elevation Level User Interfaces, Autocalibration For Joint Elevation, And Joint Pressure Estimation," which are hereby incorporated by reference in their entireties.

FIELD

The present disclosure relates generally to methods, systems, and devices for joint to pump elevation level user interfaces, autocalibration for joint elevation, and joint pressure estimation.

BACKGROUND

Arthroscopic pumps are used in a variety of surgical procedures in connection with a variety of functions, such as soft tissue ablation, contouring, cutting, coagulation, and temperature control. During performance of a surgical procedure an arthroscopic pump may provide irrigation (inflow) of fluid to a surgical site, e.g., a joint of a patient, and aspiration (outflow) of fluid from the surgical site. The pump may control fluid pressure at the joint to help provide joint distension for easy access, maintain good visibility, and/or to control bleeding. However, it is difficult for the pump to have an accurate measure of fluid pressure at the joint and, thus, for the pump to accurately control fluid pressure within the joint. For example, arthroscopic pumps typically do not measure fluid pressure at the joint but instead measure fluid pressure at the pump and make adjustments to the pump pressure to estimate fluid pressure at the joint. However, if the pump and the patient's joint are at different elevations, such as if the pump is on a cart at a higher elevation than the patient on an operating table, the fluid pressure measured at the pump will not accurately reflect the fluid pressure at the joint. Additionally, fluid travels between the pump and the joint through tubing and the sheath, but pumps may not accurately account for pressure loss in the tubing and sheath as the flow varies through the pump. Further, although an arthroscopic pump may provide an indication of measured fluid pressure at the pump, the pump does not indicate to surgeons that the measured fluid pressure is at the pump, not the joint, which may cause the surgeon to inappropriately control fluid pressure to be too high or too low at the joint since the information being provided to the surgeon does not accurately reflect actual fluid pressure at the joint.

In some systems, fluid pressure may be measured at the joint, such as with sensors positioned at the joint, but measuring fluid pressure at the joint and communicating the measured fluid pressure to the pump typically results in a significant cost increase for the disposable tube-set, which is not feasible for most hospitals and surgeons.

Accordingly, there remains a need for improved devices, systems, and methods for arthroscopic pumps.

SUMMARY

In general, methods, systems, and devices for joint to pump elevation level user interfaces, methods, systems, and devices for autocalibration for joint elevation, and methods, systems, and devices for joint pressure estimation are provided.

In one aspect, a surgical system is provided that in one embodiment includes a fluid pump system including a fluid pump. The fluid pump system is configured to pump fluid between the fluid pump and a surgical site through tubing, measure a pressure of fluid at the fluid pump, determine an estimated pressure of fluid at the surgical site by adjusting the measured pressure based on at least one of an elevation difference between the fluid pump and the surgical site and a type of the tubing, and provide an indication of the estimated pressure of fluid at the surgical site to a user of the fluid pump.

The surgical system can vary in any number of ways. For example, the fluid pump system can be configured to provide the indication of the estimated pressure by displaying the estimated pressure on a display of the fluid pump system. For another example, the fluid pump system can be configured to measure the pressure of the fluid at the fluid pump by sensing a pressure of fluid within a fluid chamber at the fluid pump.

For yet another example, the fluid pump system can be configured to receive an input from a user of the fluid pump indicative of the elevation difference. In at least some embodiments the fluid pump system can be configured to automatically prompt the user to provide the input upon startup of the fluid pump, and/or the fluid pump system can be configured to provide a visual indication of the elevation difference on a display at the pump.

For still another example, a processor of the fluid pump system can be configured to automatically determine the elevation difference. In at least some embodiments the processor can be configured to automatically determine the elevation difference upon startup of the fluid pump.

For another example, the fluid pump system can be configured to receive an input from a user of the fluid pump indicative of the tubing. For yet another example, the fluid pump system can be configured to determine the estimated pressure of fluid at the surgical site based on the type of the tubing as determined by measuring pressure based on a speed of an irrigation motor at the fluid pump. For another example, the fluid pump system can be configured to determine the estimated pressure of fluid at the surgical site also based on a type of sheath associated with the tubing as determined by measuring pressure based on a speed of an irrigation motor at the pump. For still another example, the fluid pump can be an arthroscopic fluid pump. For yet another example, the surgical site can be a joint of a patient. For another example, the fluid pump system can include a sensor configured to measure the pressure of the fluid at the fluid pump, and the fluid pump system can include a processor configured to receive the measured pressure from the sensor, determine the estimated pressure, and cause the indication to be provided to the user. For yet another example, the fluid pump can include a memory having an algorithm stored therein, and the fluid pump can include a processor configured to execute the algorithm and thereby cause the processor to determine the estimated pressure.

For another example, determining the estimated pressure can include estimating loss at an inflow to the surgical site. In at least some embodiments, estimating loss at the inflow can include determining a speed of a motor of the fluid pump.

In another aspect, a surgical method is provided that in one embodiment includes pumping fluid between a fluid pump system and a surgical site through tubing, measuring a pressure of fluid at a fluid pump of the fluid pump system, determining an estimated pressure of fluid at the surgical site by adjusting the measured pressure based on at least one of an elevation difference between the fluid pump and the surgical site and a type of the tubing, and providing an indication of the estimated pressure of fluid at the surgical site to a user of the fluid pump.

The surgical method can have any number of variations. For example, providing the indication of the estimated pressure can include displaying the estimated pressure on a display of the fluid pump system. For another example, measuring the pressure of the fluid at the fluid pump can include sensing a pressure of fluid within a fluid chamber at the fluid pump.

For yet another example, the method can include receiving at the fluid pump system an input from a user of the fluid pump indicative of the elevation difference. In at least some embodiments the method can also include the fluid pump of the fluid pump system automatically prompting the user to provide the input upon startup of the fluid pump, and/or the input can change a visual representation of relative elevation levels of the fluid pump compared to the surgical site by changing a relative position of an icon representative of a fill chamber of the fluid pump and an icon representative of the surgical site.

For another example, the method can include a processor of the fluid pump system automatically determining the elevation difference. In at least some embodiments the fluid pump system automatically determines the elevation difference upon startup of the fluid pump.

For yet another example, the method can include receiving an input from a user of the fluid pump indicative of the tubing. For another example, determining the estimated pressure of fluid at the surgical site based on the type of the tubing can include determining the measured pressure based on a speed of an irrigation motor at the fluid pump. For still another example, the fluid pump can be an arthroscopic fluid pump. For another example, the surgical site can be a joint of a patient. For yet another example, the fluid pump system can include a sensor that measures the pressure of the fluid at the fluid pump, and the fluid pump system can include a processor that receives the measured pressure from the sensor, determines the estimated pressure, and causes the indication to be provided to the user. For yet another example, the fluid pump system can include a memory having an algorithm stored therein, and the fluid pump system can include a processor configured to execute the algorithm and thereby cause the determining of the estimated pressure.

For another example, determining the estimated pressure can include estimating loss at an inflow to the surgical site. In at least some embodiments, estimating loss at the inflow can include determining a speed of a motor of the fluid pump.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for joint to pump elevation level user interfaces, methods, systems, and devices for autocalibration for joint elevation, and methods, systems, and devices for joint pressure estimation are provided. In general, an arthroscopic pump can be configured to estimate fluid pressure at a surgical site, e.g., at a joint, to provide an accurate indication of fluid pressure to users (e.g., surgeons and other medical personnel). Fluid pressure at the surgical site may therefore be accurately controlled to improve surgical outcomes. The fluid pressure at the surgical site can be accurately controlled even when an external flow device is inserted into the joint. Being able to accurately control actual joint pressure to be less than 60 mmHg may help reduce risk to the patient during the surgical procedure, such as by reducing risk of extravasation due to pressure being too high. In an exemplary embodiment, the fluid pressure estimation is based on a fluid pressure measurement at the pump that is adjusted at the pump, e.g., by a processor at the pump that executes instructions stored in a memory at the pump, using one or more control algorithms that adjust for one or more factors. One of the factors that can be used in estimating fluid pressure is pressure loss in tubing through which fluid flows between the pump and the surgical site. Another one of the factors that can be used in estimating fluid pressure is elevation difference between the pump and the surgical site. Expensive and specialized equipment, such as tubing having built-in pressure sensors, is therefore not needed to measure fluid pressure at the surgical site itself. In other words, an accurate estimation of fluid pressure at the surgical site can be determined even with fluid pressure being measured only at the pump.

Estimating losses, e.g., tubing losses and sheath losses, may allow for control of surgical site pressure by and adding them to a surgical site pressure set-point, e.g., a joint pressure set-point, to update the pump pressure set-point in a pump pressure control loop, which may be executed quickly. The control loop may therefore provide faster response and more stability than direct control of surgical site pressure.

In certain surgical setups a pump may have an elevation difference with the surgical site of six inches or more. In some cases the elevation difference can be multiple feet, such as when the pump is positioned on a cart or shelf above or below the level of the patient on an operating table. Although the pump's instructions for use (IFU) may caution against such pump positioning relative to the patient, the IFU may not always be followed, such as due to space constraints in the operating room or due to fixed cart height. In general, elevation differences between the surgical site and pump result in an error of 22.4 mmHg per foot of elevation difference. In other words, the fluid pressure measured at the pump will not accurately reflect the fluid pressure at the surgical site when the surgical site and the pump are at different elevations, with the discrepancy between the fluid pressures being increasingly greater for larger elevation differences. The ability to compensate for elevation difference and provide an accurate estimation of fluid pressure at the surgical site may greatly reduce error.

Figure 1:
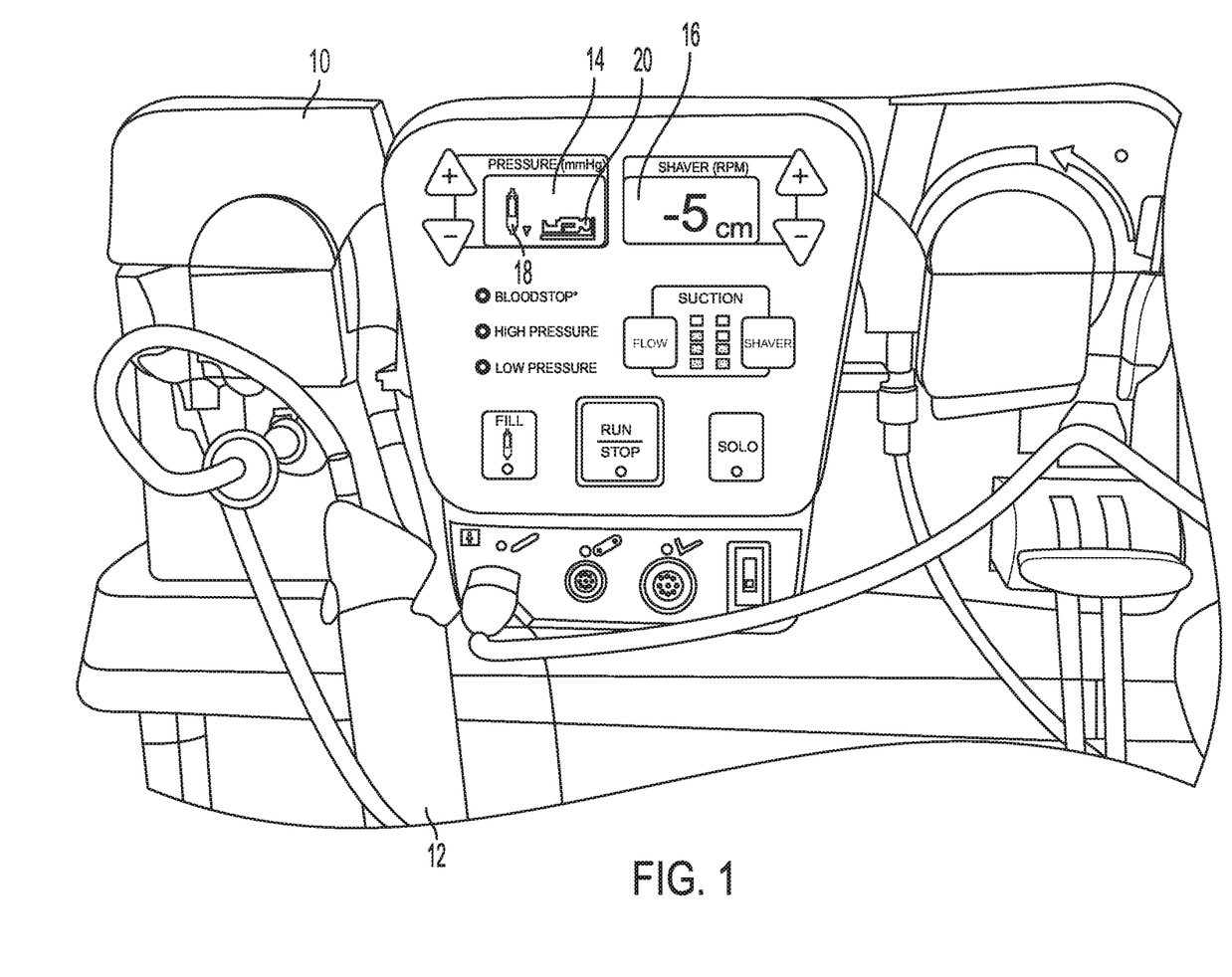
FIG. 1 is a perspective view of one embodiment of an arthroscopic fluid pump.
Figure 1A:
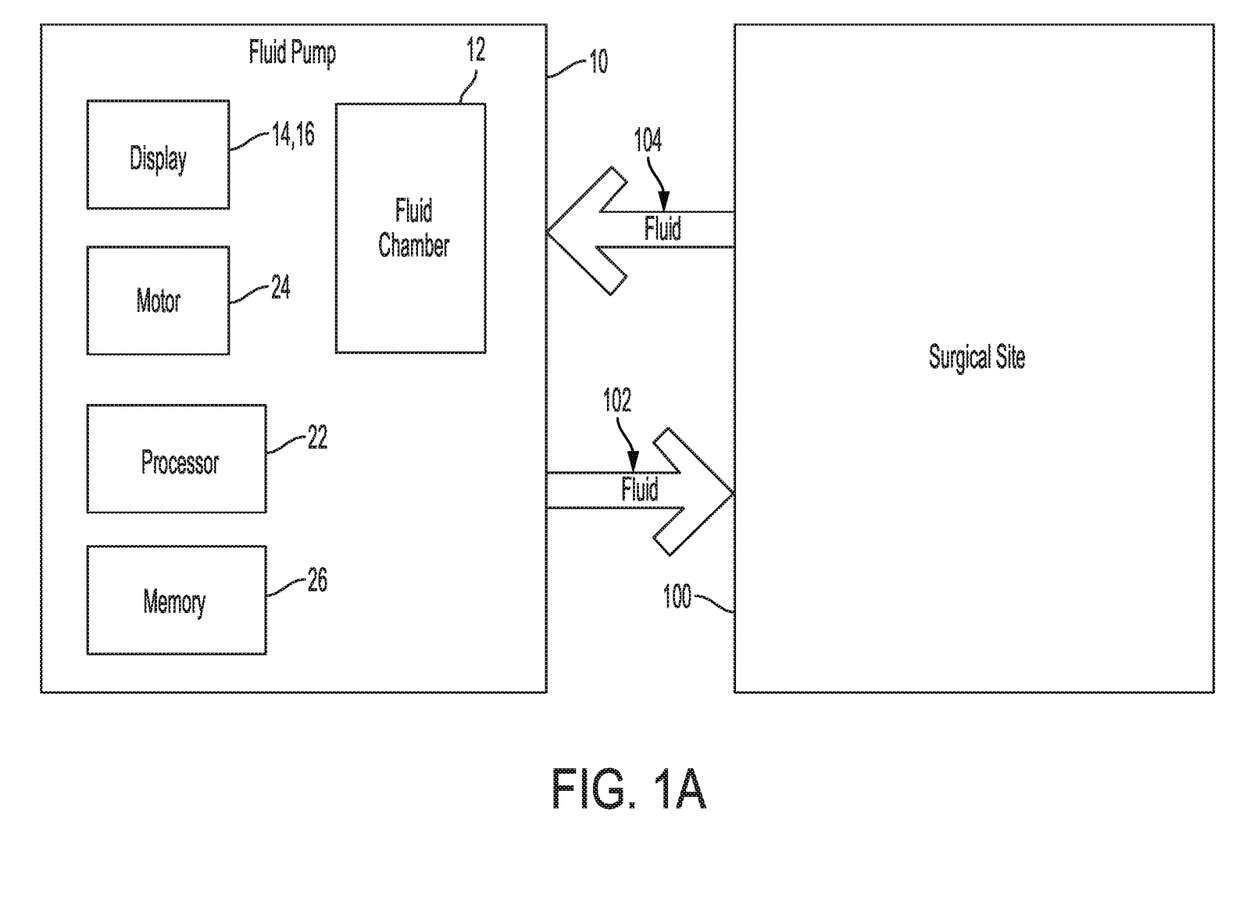
FIG. 1A is a block diagram of the pump of FIG. 1 operatively coupled to a surgical site via inflow tubing, sheath, and outflow tubing.

FIGS. 1 and 1A illustrate one embodiment of a pump system including an arthroscopic pump 10 configured to estimate fluid pressure at a surgical site 100. In an exemplary embodiment the surgical site is at a joint such as the knee or shoulder. The pump 10 is configured to estimate the fluid pressure at the surgical site 100 in real time with performance of the surgical procedure based on at least one of elevation difference between the pump 10 and the surgical site 100 and tubing through which fluid flows between the pump 10 and the surgical site 100. In an exemplary embodiment the pump 10 is configured to estimate pressure based on each of these two factors, although pressure may be estimated using only one of these factors. Each of the inflow tubing 102 and the outflow tubing 104 have an associated sheath, in which case the fluid pressure can be estimated based on the tubing 102 and its associated sheath.

The pump 10 can have a variety of configurations. In the illustrated embodiment the pump 10 includes an irrigation pump configured to pump fluid to the surgical site and includes an aspiration pump configured to pump fluid from the surgical site. The pump 10 includes joint inflow tubing to allow fluid to flow between the pump 10 and the surgical site. FIG. 1A schematically illustrates the pump 10 operatively connected to the surgical site 100 via the inflow tubing 102 and illustrates outflow tubing 104 which returns to an aspiration pump of the pump system and then to a waste reservoir. The pump 10 also includes a fill chamber or reservoir 12 which is used to smooth the fluid flow and to provide pressure sensing with the sensing tube at the top of the reservoir 12. Pressure is sensed at the fluid level, e.g., water level, in the chamber 12 so the fluid level is the effective pressure sensor location.

The pump system also includes a processor 22 that is configured to control the irrigation pump 10 and the aspiration pump. The pump 10 is configured to measure fluid pressure at the pump 10 based on fluid pressure within the reservoir 12 and on pump motor speed, e.g., a speed of a motor 24 configured to drive the pump 10. The pump 10 is configured to adjust the pressure measured at the pump 10, as controlled by the processor 22, to determine estimated pressure at the surgical site 100 using one or more control algorithms, as discussed further below. The one or more control algorithms are stored in a memory 26 of the pump system and are executable by the processor 22. The processor 22 and the memory 26 are shown as part of the pump 10 in FIG. 1A, but in other embodiments the processor 22 and/or the memory 26 can be located elsewhere in the pump system.

The pump system also includes a user interface configured to facilitate user interaction with the pump 10. The user interface includes a first display 14 configured to display joint pressure (in mmHg in this illustrated embodiment) in real time with use of the pump 10 during performance of a surgical procedure. The fluid pressure shown on the first display 14 is the estimated pressure of fluid at the surgical site. The user interface also includes a second display 16 configured to display shaver speed (in revolutions per minute (RPM) in this illustrated embodiment).

The user interface also includes user controls configured to receive input from the user to control various pump functions. In the illustrated embodiment the user controls include depressible+/−(up/down) arrow buttons to control adjustment of information on the first display 14, and depressible+/−(up/down) arrow buttons to control adjustment of information on the second display 16. In other embodiments controls other than buttons may be used for one or both of the displays 14, 16, such as knobs, dials, levers, a keypad, or the like. Aspiration pump flow rates are controlled by buttons labelled FLOW+ and SHAVER. The FLOW+ flow button is configured to be activated with a foot pedal, and the SHAVER flow button is configured to be activated when a shaver is enabled. The illustrated embodiment also includes a key that enables filling of the fill chamber 12 and a key that enables SOLO (irrigation pump only) mode. In other embodiments one or both of the FLOW+ and SHAVER buttons can have another form, such knobs, dials, levers, or the like. The illustrated user interface also includes lights, e.g., light-emitting diodes (LEDs) or the like, that illuminate to indicate various conditions such as bloodstop, high pressure warning, low pressure alarm, FLOW+ flow rate, SHAVER flow rate, chamber fill enabled, and pump on/off (run/stop).

As mentioned above, the pump 10 can be configured to estimate pressure by taking into consideration the elevation difference between the pump 10 and the surgical site 100. The user interface in the illustrated embodiment is configured to facilitate the pump's compensation for elevation differences between the pump 10 and the surgical site 100.

The first display 14 is configured to show thereon an elevation icon indicating relative elevation of the pump 10 and the patient. The elevation icon in this illustrated embodiment is International Organization for Standardization (ISO) compliant. As shown in FIG. 1, the elevation icon includes a pump fill chamber icon 18 in the form of a pump fill chamber with a fill level and an ISO approved patient icon 20 in the form of a patient on an operating table, although other forms of elevation icons can be used. The fill level is indicative of the level where pressure is being sensed. For example, the fill chamber icon in FIG. 1 shows the fill chamber partially filled, and it is this fill level that indicates the level where pump pressure is sensed, e.g., the zero-elevation level. The elevation difference between the pump 10 and the surgical site 100 is defined with respect to the zero-level elevation, with the surgical site 100 either being at the zero-level elevation (e.g., no elevation difference), below the zero-level elevation, or above the zero-level elevation.

The second display 16 is configured to show the elevation difference between the pump 10, e.g., the fill level of the fill chamber 12, and the surgical site 100 at the patient. The patient icon 20 on the second display 16 is configured to be in one of three positions relative to the pump fill chamber icon 18 to indicate whether the surgical site 100 is elevated above the fill chamber 12 (patient icon 20 in an upper position), the surgical site 100 is at a same elevation as the fill chamber 12 (patient icon 20 in a middle or neutral position), or the surgical site 100 is lower than the fill chamber 12 (patient icon 20 in a lower position). In the illustrated embodiment, as shown in FIG. 1, the second display 16 shows the elevation difference between the fill level of the fill chamber 12 and the surgical site 100 as being −5 cm, indicating that the surgical site 100 is 5 cm lower than the pump 10. The patient icon 20 is thus in a lower position relative to the pump fill chamber icon 18 on the first display 14. In other embodiments, more granular positions of the patient icon 20 may be used by having more than three possible positions of the patient icon 20 relative to the pump fill chamber icon 18. For example, five positions may be possible for the patient icon 20 relative to the pump fill chamber icon 18: a position indicating that the surgical site 100 is at a same elevation as the fill chamber 12, a first higher position indicating an elevation above a first predetermined threshold elevation difference, a second higher position indicating an elevation above a second predetermined threshold elevation difference that is greater than the first predetermined threshold elevation difference, a first lower position indicating an elevation lower than a third predetermined threshold elevation difference, and a second lower position indicating an elevation lower than a fourth predetermined threshold elevation difference that is greater than the third predetermined threshold elevation difference.

Figure 2:
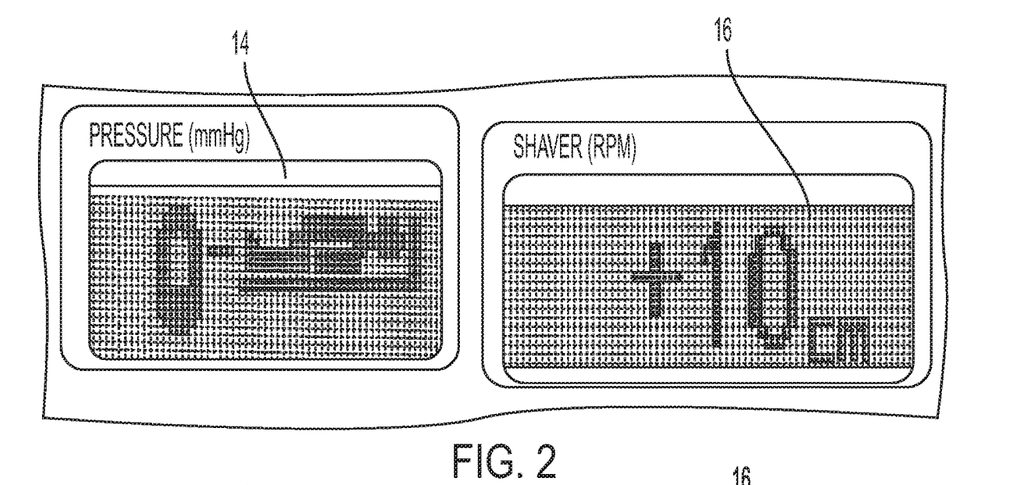
FIG. 2 is a display of the fluid pump of FIG. 1 showing one elevation difference between the fluid pump and a patient.
Figure 3:
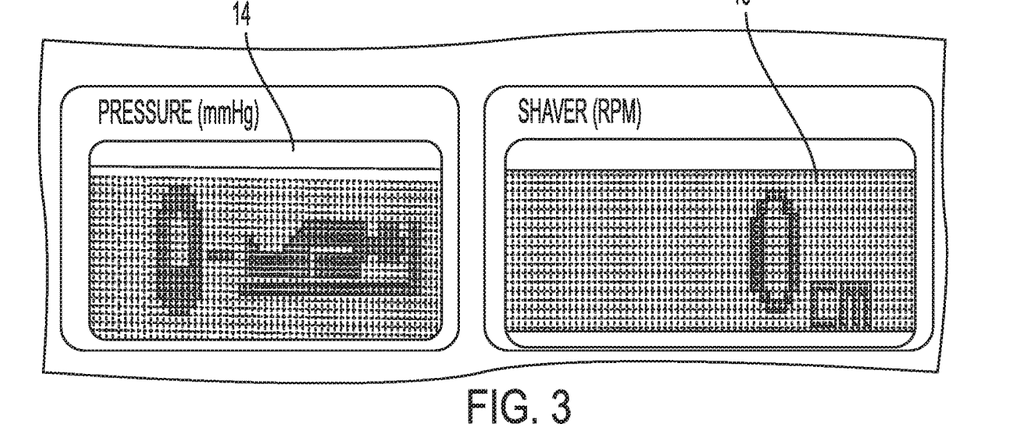
FIG. 3 is the display of the fluid pump of FIG. 1 showing another elevation difference between the fluid pump and a patient.
Figure 4:
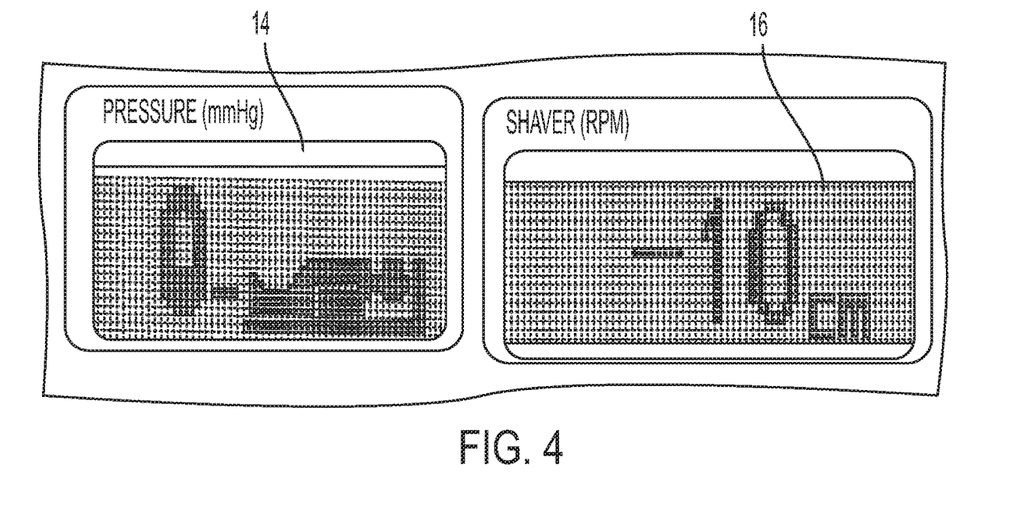
FIG. 4 is the display of the fluid pump of FIG. 1 showing yet another elevation difference between the fluid pump and a patient.

The user interface is configured to allow a user to adjust the elevation difference using the +/− arrows associated with the first display 14 or, alternatively, the +/− arrows associated with the second display 16. For example, each push of the + arrow can increase the elevation difference by a predetermined amount, e.g., 1 cm, 2 cm, 5 cm, 10 cm, etc., and each push of the − arrow can decrease the elevation difference by a predetermined amount, e.g., 1 cm, 2 cm, 5 cm, 10 cm, etc. As the elevation difference is adjusted, the patient icon 20 moves up/down accordingly to provide visual indication of the patient's elevation relative to the pump 10, and in particular relative to the fluid level in the fill chamber 12 of the pump 10. A positive, non-zero elevation difference indicative of the fill level of the fill chamber 12 being above the surgical site 100 can be shown with the patient icon 20 an upper position relative to the pump fill chamber icon 18 on the first display 14, and in particular relative to the fluid level mark on the pump fill chamber icon 18. For example, FIG. 2 shows an elevation difference of +10 cm on the second display 16 and the patient icon 20 thus in the upper position. A zero elevation difference can be shown with the patient icon 20 a middle or neutral position relative to the pump fill chamber icon 18 on the first display 14, and in particular relative to the fluid level mark on the pump fill chamber icon 18. For example, FIG. 3 shows an elevation difference of 0 cm on the second display 16 and the patient icon 20 thus in the middle or neutral position. A negative, non-zero elevation difference indicative of the fill level of the fill chamber 12 being below the surgical site 100 can be shown with the patient icon 20 a lower position relative to the pump fill chamber icon 18 on the first display 14, and in particular relative to the fluid level mark on the pump fill chamber icon 18. For example, FIG. 4 shows an elevation difference of −10 cm on the second display 16 and the patient icon 20 thus in the lower position. Elevation difference may be higher than +10 cm or less than −10 cm. For example, elevation difference may be in a range from −60 cm to +90 cm.

The user interface is configured to show the elevation icon on the first display 14 upon startup of the pump 10. For example, when power is turned on or when the run/stop button is pushed to signal pump "on," the user is prompted by instruction on one or both of the displays 14, 16 and/or by audible instruction through a speaker operatively connected to the pump 10 to confirm relative elevation of the surgical site 100 and pump 10, in particular the fill level of the pump's chamber 12. The user confirms the relative elevation by adjusting elevation as needed using the +/− arrows associated with the first display 14. The system may thus have accurate relative elevation information that the processor 22 can later use in estimating fluid pressure at the surgical site 100. To accept the displayed elevation as accurate, the user presses the run/stop button. After the user's manual input of the relative elevation, the first display 14 can continue displaying the elevation icon or can instead display a numerical value of fluid pressure, and the second display 16 can continue displaying elevation level or can instead display a numerical value of shaver speed. Another press of the run/stop button starts the irrigation pump and the aspiration pump.

In at least some embodiments, a measurement device can be provided that is configured to facilitate the user's input of elevation difference to the pump 10. For example, the pump 10 can have a mechanical measurement device mounted thereon, e.g., a ruler or the like, that a user can extend from the pump 10 to the surgical site 100 to allow measurement of surgical site elevation using line of sight. The mechanical measurement device mounted to the pump 10 can be retractable (similar to a tape measure) to facilitate storage and/or ease of use. For another example, the pump 10 can have a mechanical measurement device mounted thereon as described above in addition to a level laser light source to facilitate measurement of surgical site elevation. The level laser light source can be located, for example, at the end of the mechanical measurement device. For yet another example, a mechanical measurement device can be mounted on a cart on which the pump 10 sits and can be extended from the cart to the surgical site to allow measurement of surgical site elevation using line of sight. The mechanical measurement device mounted to the cart can be retractable (similar to a tape measure) to facilitate storage and/or ease of use. For still another example, the pump 10 can have a slide mounted thereon that has a linear encoder (magnetic or optical) mounted thereon. The slide can be selectively movable up and down by a user to align an end of the slide with the surgical site 100 using line of sight, with the linear encoder measuring position. For another example, the pump 10 can have a slide as described above in addition to a level laser light source to facilitate measurement of surgical site elevation. The slide can be selectively movable up and down by a user to align a light beam (e.g., from the light source such as a laser point) with the surgical site 100, with the linear encoder measuring position. For yet another example, the pump 10 can include a laser interferometer configured to measure elevation difference between the pump 10 and the surgical site 100.

In at least some embodiments, rather than a user manually input elevation difference between the pump 10 and the surgical site 100, the pump 10 is configured to automatically determine elevation distance between the pump 10 and the surgical site 100. In such an embodiment, the pump 10 is configured to automatically determine elevation on startup of the pump 10 so the pump 10 has the relevant information needed to adjust fluid pressure in view of the elevation difference when the pump 10 is in use. In general, to automatically determine elevation the pump 10 can be configured to zero the pressure at the level of the surgical site 100 to allow for compensation of any elevation difference between the surgical site 100 and the pump 10.

In one embodiment of pump autocalibration, at pump startup, the user will press the run/stop button on the pump's user interface. An icon will then show on the first display 14 and/or the second display 16 indicating that a pressure calibration will occur. The user will hold the sheath connected to the end of the irrigation tubing 102 that runs between the pump 10 and the surgical site 100 at the level of the surgical site 100, e.g., at joint level, with the pump's irrigation valve open and then press the run/stop button for the second time. The pump 10 can be configured to prompt the user to hold the sheath at the level of the surgical site 100, such as by instruction on one or both of the displays 14, 16 and/or by audible instruction through a speaker operatively connected to the pump 10. The pump's irrigation pump will then function in flow control mode for sufficient time for it to prime. At this time, the pressure will be recorded for a predetermined amount of time, e.g., a few tenths of a second, and averaged. Then the irrigation flow will be increased to provide another pressure data point. These two pressure versus flow data points will be used by the pump 10, e.g., a processor 22 thereof, in a control algorithm to estimate the elevation of the surgical site 100 relative to the pump 10 as well at the losses in the tubing and sheath. The results of the algorithm will then be limit checked by the pump 10, e.g., by the processor 22 thereof, and if the results are within a predetermined tolerance, the pump 10 will end the autocalibration. The end of autocalibration may be indicated by the pump 10, such as with audible sound such as a beep and/or with a visual on one or both of the displays 14, 16. At the end of autocalibration, depressing the run/stop button will allow the user to adjust the joint pressure set-point and shaver RPM speed set-point. Another press of the run/stop button will start the pump 10 in its normal pressure regulation mode.

As mentioned above, in addition to or instead of the pump 10 estimating pressure by taking into consideration the elevation difference between the pump 10 and the surgical site 100, the pump 10 can be configured to estimate pressure by taking into consideration the tubing 102, 104 and, if present, the sheaths associated with the tubing 102, 104. In at least some embodiments the pump 10 can be configured to allow a user to input tubing size and/or sheath size. The pump 10 can be configured to use the input size in evaluating pressure loss compensation due to the tubing and sheath that runs between the pump 10 and the surgical site 100. For example, the pump's user interface can include a depressible sheath size control button that allows the user to use the +/− arrows associated with the first display 14 or the second display 16 to adjust sheath size up/down to reflect the current sheath size. Depressing the sheath size control button again can indicate acceptance of the displayed sheath size. In general, although high flow sheaths are used in most arthroscopic surgeries, smaller low flow sheaths are typically used for small joints and result in reduced accuracy in joint pressures. Thus, allowing input of sheath size will allow the pump 10 to compensate for sheath size in estimating fluid pressure at the surgical site. In other embodiments a control other than a button may be used for inputting sheath size, such as knobs, dials, levers, a keypad, or the like. In addition to or instead of a depressible sheath size control button, the pump's user interface can include a depressible tubing size control button that allows the user to use the +/− arrows associated with the first display 14 or the second display 16 to adjust tubing size up/down to reflect the current tubing size similar to that discussed above regarding the input of sheath size. In other embodiments a control other than a button may be used for inputting tubing size, such as knobs, dials, levers, a keypad, or the like.

Figure 5:
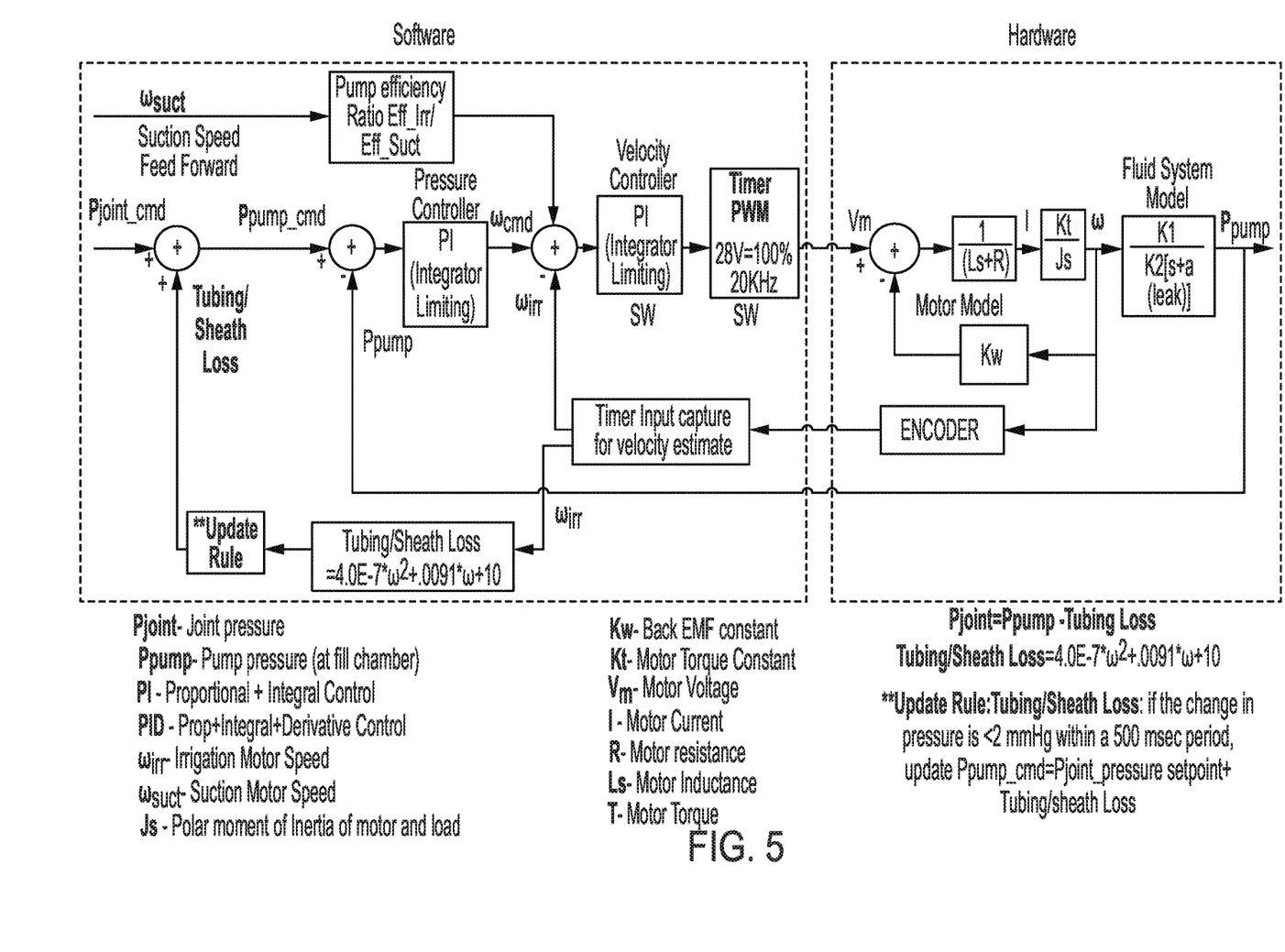
FIG. 5 is a block diagram showing one embodiment of a fluid control algorithm of the pump of FIG. 1.

One embodiment of a control algorithm that the pump system can use to estimate and control fluid pressure based on at least tubing loss and sheath loss is described below with respect to FIG. 5. In an exemplary embodiment, as shown in FIG. 5, the control algorithm is implemented in a combination of software and hardware. The processor 22 is configured to execute the control algorithm using various electronic components, as will be appreciated by a person skilled in the art, such as pump components of a rotary encoder, motor/gearbox, pressure transducer, and interface/control circuits.

The algorithm first determines a pump pressure set-point by estimating tubing/sheath losses and adding this pressure drop to the joint pressure set-point. A pump pressure control loop is then controlled using a proportional plus integral (PI) controller. Additionally, feedforward control from the suction pump is applied to anticipate sudden flow changes induced by the aspiration pump, such as flow+ and shaver flows. The pressure control signal (from the PI controller) combined with the feedforward signal from the suction pump provide a velocity command to an irrigation velocity control loop. FIG. 5 illustrates the irrigation pump control loop. The pump pressure set-point is updated based on the estimated losses in the tubing and sheath. The estimation algorithm is updated on a regular basis as opposed to only when changing flow mode. The regular basis can be any of a variety of predetermined intervals during use of the pump system, such as every X seconds, every Y minutes, etc.

The irrigation pump is configured to control the pressure at the surgical site, e.g., in the surgical joint where arthroscopic surgery is being performed. However, pressure is not measured at the joint but only at the pump, e.g., in the fill chamber. So, to regulate joint pressure, tubing/sheath losses are estimated and then added to the desired joint pressure $P_{joint\_cmd}$, e.g., the pressure set-point previously input to the pump and/or as preset at the pump, to provide the updated pump pressure set-point $P_{pump\_cmd}$. The basis for adding desired joint pressure to tubing/sheath loss to produce the updated pump pressure set-point is that the pump pressure is equal to the joint pressure plus the tubing/sheath pressure drop. The tubing/sheath losses are a function of flow and are therefore a function of a speed of the pump system's irrigation motor. The algorithm therefore takes motor speed w into account to estimate fluid pressure at the surgical site, e.g., at the joint. The estimator for tubing/sheath loss is as follows, where ω=angular velocity of irrigation motor in EncoderCnts/sec:

Tube/Sheath Loss [mmHg]=4.70*ω²+0.0091*ω+10

Angular velocity is calculated by using the irrigation encoder interrupt to determine time between successive encoder pulses (identical to the suction pump velocity calculation). Velocity in encoder counts per second is determined as follows:

Velocity=1406250 [clkPulses/sec]/time between Encoder pulses

When the timer interrupt has not occurred for 5 milliseconds (10 times through 2 KHz timer interrupt), the velocity will be reported as zero. The velocity command is updated on a regular basis as the output of the pressure loop PI (Proportional, Integral) controller used for pressure regulation. The regular basis can be any of a variety of predetermined intervals during use of the pump system, such as every X seconds, every Y minutes, etc. The pressure control system uses the same velocity control strategy as for the suction pump, so the pressure controller (PI) provides a velocity command to the velocity control loop and this update is used in the controller calculations. The pressure loop PI controller is updated in the 2 KHz timer interrupt which is also used for control of the suction pump and the shaver. However, the pressure control algorithm is only updated every 64 times through the ISR (interrupt service routine) which is equal to 32 msec. This is sufficient due to the low closed loop bandwidth of the pressure control loop (i.e., <2 Hz). The PI controller equations are as follows, where Kp=400, Ki=0.222, Kd=0.0, suctionFeedForward=suction speed*efficiency ratio of irrigation/suction pump:

setPointPumpPress=setPointJointPress+TubeSheath-Loss $P$control=error*$Kp$+SUM_ERROR*$Ki$−$Kd$*$d$Err VELCMD=$P$control+suctionFeedForward To determine the updated pump pressure set-point, the above equation is executed on a regular predetermine basis, e.g., every 32 msec, however, the TubeSheathLoss is only updated when the pump pressure has settled: If successive readings (spaced at, e.g., 500 msec) are within, e.g., 2 mmHg of each other.

A control loop is used for regulating the angular velocity of the suction (aspiration) pump. While both current and velocity feedback can be used, current feedback is not required. The controller output provides a PWM duty cycle to the motor using a 20 KHz PWM output compare timer. Additionally, a rate limit is provided to the PWM outputs so that pulses are ramped at each transition to eliminate the pulsing of the motor at 2 KHz which would certainly be audible. The rate limit is 10 encoderCnts/2 KHz interrupt. This means that the motor can go from zero to max speed within 0.8 seconds.

To improve response time to shaver or Flow+ step changes in suction flow, a motor velocity feedforward term is provided from the suction motor speed command. This helps the joint pressure control loop to anticipate local (i.e., caused by this pump) flow disturbances such as enabling or disabling the shaver or flow+. Suction speed feedforward is multiplied by the pump efficiency ratio to provide the correct steady state feedforward flow compensation in the irrigation pump to offset the additional flow in the suction pump. A ramp is applied to the suction feedforward speed to try to offset the speed ramp in the suction pump used for shaver and Flow+ flows. Feedforward suction speed compensation is combined with the output of the PID controller to provide a velocity command to the velocity control loop used for the irrigation pump. This velocity control loop is identical to the suction pump.

To prevent annoyance of rapid updates of the joint pressure displayed, the pressure displayed is the estimated joint pressure updated every half second and additional filtering. The factory default joint pressure setting is 70 mmHg, although the default can be updated by the user with the default menu. In other implementations, the factory default pressure setting is 50 mmHg.

Suction pump operation only requires the user to press the RUN button, as long as SOLO mode is not selected and a door of the pump system is closed. This is assuming that no faults exist such an over-current for the pump motors.

The irrigation (inflow) pump control uses a 2 KHz timer and two separate control mechanisms pressure (two pressure sensors) and velocity (high speed encoder) to control the motor speed. FIG. 5 shows the overall control loop for regulating the pressure.

When the pump is in RUN mode, the 2 KHz loop along with the state-chart processing below performs the following: (1) The pressure controller uses the readings from two analog channels (ADC) to determine the difference between the pressure set-point and the actual pressure read at the pressure sensors. These signals are read and averaged together. Based on this difference (error) the new command PWM duty cycle counts value that is fed into the velocity portion of the motor control loop is determined; and (2) the velocity controller uses the feedback from the high-speed encoder (frequency) which is tied to an Input Capture Compare Timer. Using the command counts determined in the previous step and the speed frequency of the motor a new duty cycle to the PWM command input is calculated. This command is then fed into the PWM control register associated with the Inflow motor. The PWM frequency is, e.g., 20 Khz. The two pressure signals are monitored and compared to ensure that they are accurate within a predetermined threshold, e.g., +/−10%, from each other.

Figure 6:
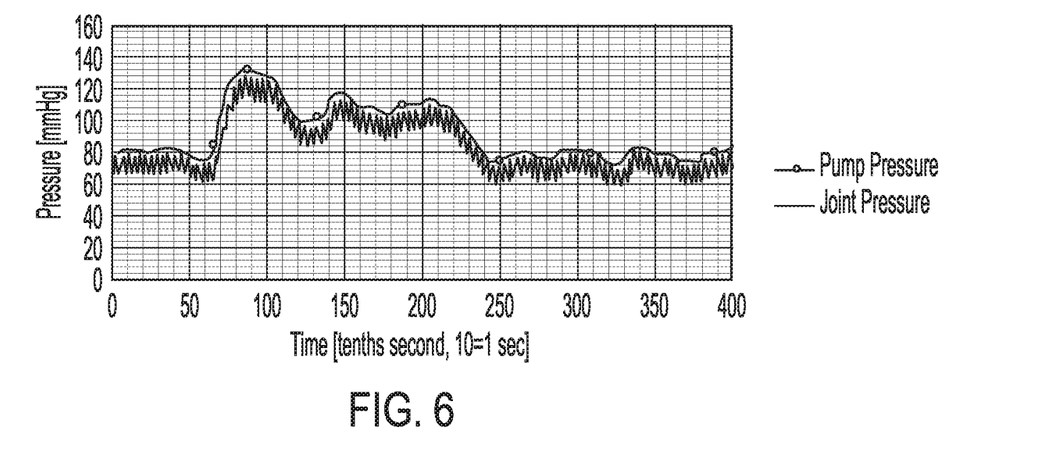
FIG. 6 is a graph showing fluid pressure versus time.
Figure 7:
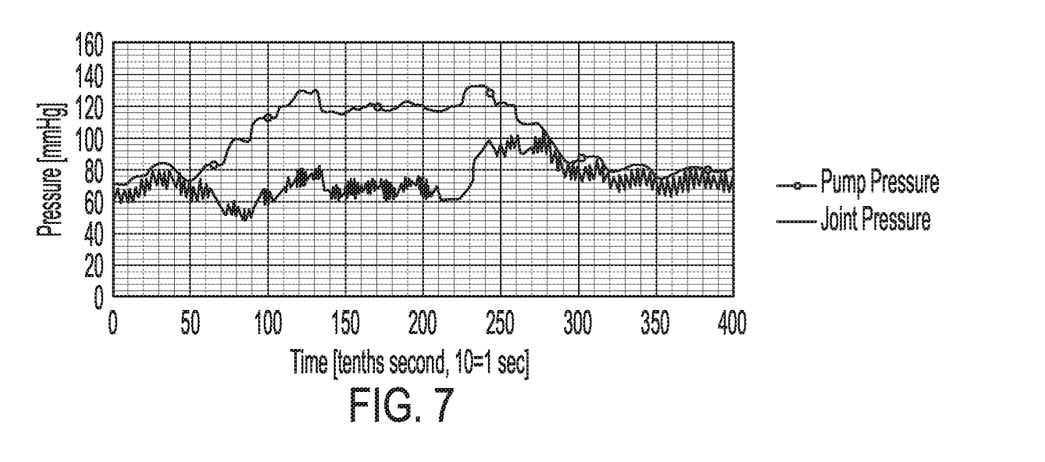
FIG. 7 is still another graph showing fluid pressure versus time.
Figure 8:
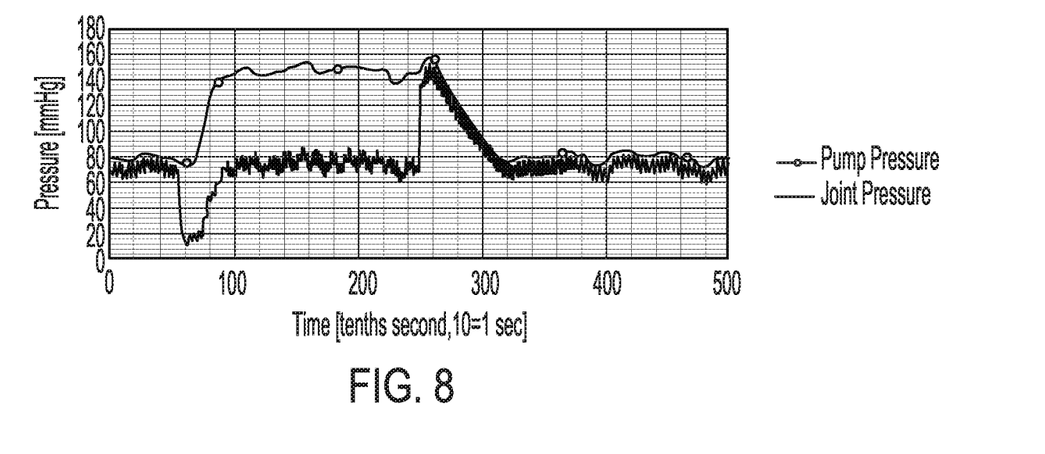
FIG. 8 is another graph showing fluid pressure versus time.

FIGS. 6-8 are graphs showing various scenarios in which fluid pressure at the pump, e.g., pressure measured at the fill level of the pump's fill chamber, differs from fluid pressure at the surgical site. These illustrated differences between pressure at the pump and pressure at the surgical site help highlight the importance of estimating pressure at the surgical site instead of considering pressure measured at the pump to be an accurate reflection of pressure at the surgical site.

FIG. 6 is a graph showing pressure (in mmHg) versus time (in tenths of a second) in response to a 30 mmHg step (70 mmHg to 100 mmHg) for pressure at the fluid pump and estimated pressure at the surgical site (which is a joint in this embodiment) calculated by the fluid pump with compensation for elevation and tubing/sheath losses. The graph shows that the pressure at the fluid pump differs only slightly from the estimated pressure at the surgical site.

FIG. 7 is a graph showing pressure (in mmHg) versus time (in tenths of a second) in response to a step change in flow of about 350 mL/min due to an internal shaver suction source active from about 5 sec to about 250 sec. The graph shows that the pressure at the fluid pump increases as flow increases in order to regulate joint pressure while the shaver is enabled.

FIG. 8 is a graph showing pressure (in mmHg) versus time (in tenths of a second) in response to a step change in flow of about 350 mL/min due to an external suction source active from about 5 sec to about 25 sec. The graph shows that the pressure at the fluid pump increases to regulate the pressure at the surgical site.

Figure 9:
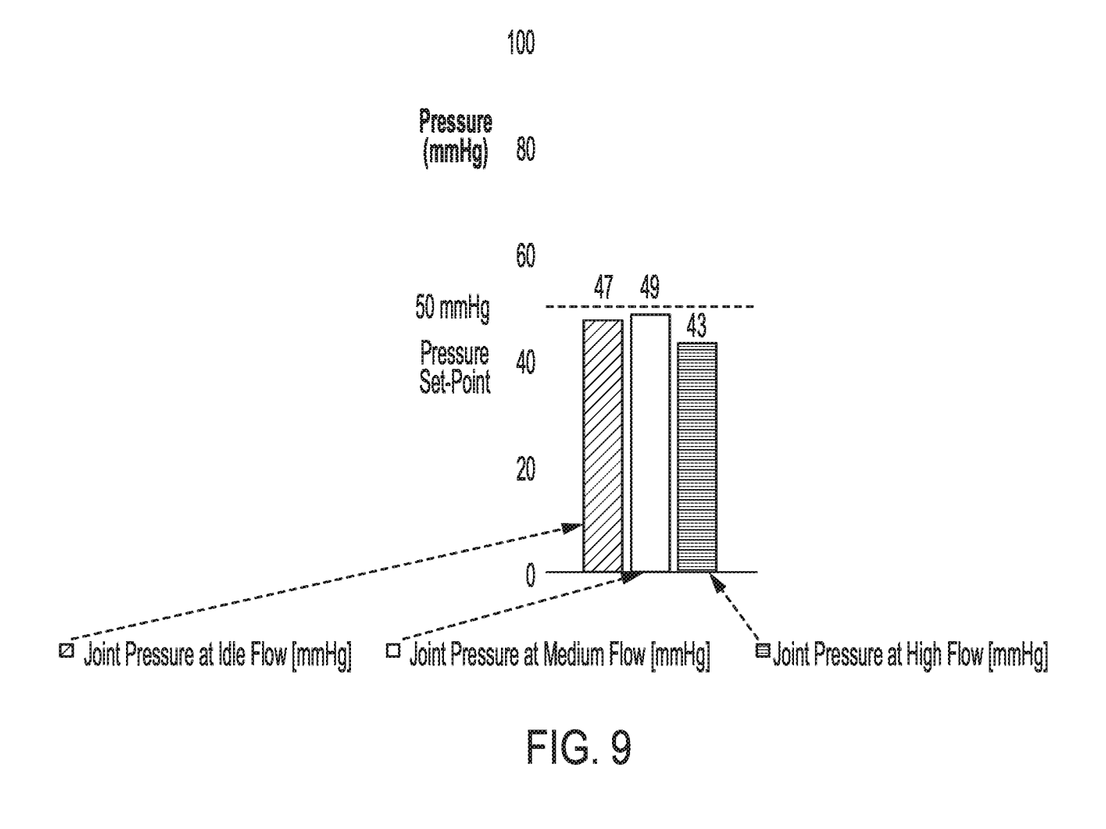
FIG. 9 is a graph showing fluid pressure at three different fluid flow rates.

FIG. 9 is a graph demonstrating the effectiveness of controlling fluid pressure at the surgical site using the fluid pressure estimation that is described herein. The graph of FIG. 9 shows pressure (in mmHg) at three different fluid flow rates: idle flow, medium flow, and high flow. The graph shows that by estimating fluid pressure at the surgical site as described herein, the fluid pressure at the surgical site can be accurately controlled to allow surgeons to use a lower pressure set-point, which may help improve patient safety, e.g., help reduce the risk of extravasation or otherwise help improve patient safety, by maintaining fluid pressure at a safe level. The pressure set-point in this example is 50 mmHg, and the site pressure in this example is 47 mmHg at idle flow, 49 mmHg at medium flow, and 43 mmHg at high flow, which is very good pressure regulation over such a flow range.

A person skilled in the art will appreciate that the present invention has application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
  pumping fluid between a fluid pump and a surgical site;
  measuring a fluid pressure fluid at the fluid pump;
  determining an estimated pressure of fluid at the surgical site by adjusting the measured pressure based on an elevation difference between the fluid pump and the surgical site; and
  displaying the estimated pressure on a display.

2. The method of claim 1, further comprising receiving at the fluid pump an input from a user of the fluid pump, the input being indicative of the elevation difference.

3. The method of claim 2, further comprising, in response to receiving the input, changing a visual representation of relative elevation levels of the fluid pump compared to the surgical site by changing a relative position of an icon on the display that is representative of a fill chamber of the fluid pump and an icon on the display that is representative of the surgical site.

4. The method of claim 1, further comprising automatically determining, using a processor of the fluid pump, the elevation difference.

5. The method of claim 4, further comprising, based on the determined elevation difference, changing, using the processor, a visual representation of relative elevation levels of the fluid pump compared to the surgical site by changing a relative position of an icon on the display that is representative of a fill chamber of the fluid pump and an icon on the display that is representative of the surgical site.

6. The method of claim 1, wherein a sensor measures the fluid pressure, and a processor receives the measured pressure from the sensor, determines the estimated pressure, and causes the estimated pressure to be displayed.

7. The method of claim 1, wherein determining the estimated pressure includes estimating loss at an inflow to the surgical site.

8. The method of claim 1, wherein the fluid is pumped between the fluid pump and the surgical site through tubing; and
  the measured pressure is also adjusted based on a size of the tubing.

9. The method of claim 8, further comprising receiving, via a user interface, an input from a user of the fluid pump, the input being indicative of the size of the tubing.

10. The method of claim 8, wherein determining the estimated pressure of fluid at the surgical site based on the size of the tubing includes determining the measured pressure based on a speed of a motor that drives the pumping through the tubing.

11. The method of claim 1, wherein the fluid pump is an arthroscopic fluid pump; and
  the surgical site is a joint of a patient.

12. A surgical method, comprising:
  pumping fluid between a fluid pump and a surgical site through tubing;
  measuring a fluid pressure at the fluid pump;
  determining an estimated pressure of fluid at the surgical site by adjusting the measured pressure based on a size of the tubing; and
  displaying the estimated pressure on a display;
  wherein the fluid is pumped from a fluid reservoir; and
  the measured pressure is also adjusted based on an elevation difference between the fluid reservoir and the surgical site.

13. The method of claim 12, further comprising receiving at the fluid pump an input from a user of the fluid pump, the input being indicative of the size of the tubing.

14. The method of claim 12, wherein the fluid pump is an arthroscopic fluid pump; and
  the surgical site is a joint of a patient.

15. A surgical system, comprising:
  a fluid reservoir configured to contain an irrigation fluid therein;
  tubing configured to be in fluid communication with the fluid reservoir;
  a motor configured to cause the irrigation fluid to be pumped out of the fluid reservoir and through the tubing to a surgical site;
  a sensor configured to measure a pressure of the irrigation fluid in the fluid reservoir; and
  a processor configured to determine an estimated fluid pressure at the surgical site based on the measured pressure and on an elevation difference between the fluid reservoir and the surgical site.

16. The system of claim 15, further comprising a display; wherein the processor is configured to cause the display to show an indication of the estimated fluid pressure.

17. The system of claim 15, further comprising a memory configured to store an algorithm therein;

wherein the processor is configured to execute the algorithm to determine the estimated pressure.

18. The system of claim 15, wherein the processor is configured to automatically determine the elevation difference.

19. The system of claim 15, further comprising a user interface configured to receive the elevation difference via a user input to the user interface.

20. The system of claim 15, wherein the processor is also configured to determine the estimated fluid pressure at the surgical site based on a size of the tubing.

* * * * *